(12) United States Patent
Sinatra et al.

(10) Patent No.: US 9,198,881 B2
(45) Date of Patent: Dec. 1, 2015

(54) EQUINE NUTRITIONAL SUPPLEMENT

(76) Inventors: Stephen T. Sinatra, Manchester, CT (US); Stanley N. Jankowitz, Franklin Lakes, NJ (US)

( * ) Notice: Subject to any disclaimer, the term of this patent is extended or adjusted under 35 U.S.C. 154(b) by 0 days.

(21) Appl. No.: 13/353,169

(22) Filed: Jan. 18, 2012

(65) Prior Publication Data

US 2012/0183521 A1  Jul. 19, 2012

Related U.S. Application Data

(60) Provisional application No. 61/433,742, filed on Jan. 18, 2011.

(51) Int. Cl.

| | | |
|---|---|---|
| A61K 36/324 | (2006.01) | |
| A61K 36/9066 | (2006.01) | |
| A61K 31/122 | (2006.01) | |
| A23K 1/16 | (2006.01) | |
| A23K 1/18 | (2006.01) | |
| A61K 31/121 | (2006.01) | |
| A61K 31/205 | (2006.01) | |
| A61K 31/7004 | (2006.01) | |

(52) U.S. Cl.
CPC ............. *A61K 31/122* (2013.01); *A23K 1/1609* (2013.01); *A23K 1/1612* (2013.01); *A23K 1/1643* (2013.01); *A23K 1/1806* (2013.01); *A61K 31/121* (2013.01); *A61K 31/205* (2013.01); *A61K 31/7004* (2013.01); *A61K 36/324* (2013.01)

(58) Field of Classification Search
USPC .................................................. 424/725, 756
IPC ....................................... A61K 36/324,36/9066
See application file for complete search history.

(56) References Cited

U.S. PATENT DOCUMENTS

| 6,503,506 B1 | 1/2003 | Germano | |
|---|---|---|---|
| 8,343,517 B1 * | 1/2013 | Bezzek .......................... | 424/400 |
| 2002/0182196 A1 * | 12/2002 | McCleary ..................... | 424/94.1 |
| 2002/0183263 A1 | 12/2002 | Hageman et al. | |
| 2005/0002992 A1 * | 1/2005 | McCleary et al. ............. | 424/439 |
| 2006/0062859 A1 * | 3/2006 | Blum et al. ..................... | 424/725 |
| 2007/0154575 A1 * | 7/2007 | Shimoda et al. ............... | 424/756 |
| 2008/0020018 A1 * | 1/2008 | Moodley et al. ............... | 424/433 |
| 2008/0113031 A1 * | 5/2008 | Moodley et al. ............... | 424/490 |
| 2008/0213246 A1 * | 9/2008 | Ziff et al. ..................... | 424/94.65 |
| 2009/0246314 A1 | 10/2009 | Montague | |
| 2010/0055218 A1 * | 3/2010 | Raederstorff et al. ........ | 424/765 |
| 2011/0305765 A1 * | 12/2011 | Mathur et al. ................. | 424/491 |

OTHER PUBLICATIONS

Dallas Clouatre, Ph.D., "L-Carnitine with a focus on muscle and energy", Total Health, vol. 27, No. 1, pp. 42, 43.

* cited by examiner

*Primary Examiner* — Chris R Tate
(74) *Attorney, Agent, or Firm* — Michael P. Kochka, Esq.

(57) ABSTRACT

A nutriceutical supplement for use in equines provides enhanced mitochondrial energizing activity and reduced inflammation and results in enhanced resistance to training injuries and diseases and enhances peak racing performance. The supplement is provided along with equine feed as a formulation including at least Coenzyme Q10, Carnitine, d-Ribose, Boswellia extract and Curcumin. These ingredients provide enhanced mitochondrial energizing activity and reduced stress, inflammation and injuries.

3 Claims, 6 Drawing Sheets

| Condition | Exercise** | Time | Lactate (mean) | Lactate (SEM) | MDA (mean) | MDA (SEM) |
|---|---|---|---|---|---|---|
| Placebo | | 0 rest | 0.642 | 0.056 | 0.649 | 0.060 |
| Placebo | 1 | pre ex | 0.608 | 0.026 | 0.718 | 0.076 |
| Placebo | 1 | 0 post ex | 1.333 | 0.129 | 0.799 | 0.068 |
| Placebo | 1 | 2 hr post ex | 0.650 | 0.034 | 0.702 | 0.064 |
| Placebo | 2 | pre ex | 0.642 | 0.034 | 0.817 | 0.106 |
| Placebo | 2 | 0 post ex | 16.000 | 2.033 | 0.855 | 0.067 |
| Placebo | 2 | 2 hr post ex | 0.900 | 0.118 | 0.668 | 0.061 |
| Placebo | 3 | pre ex | 0.750 | 0.056 | 0.779 | 0.051 |
| Placebo | 3 | 0 post ex | 20.938 | 0.391 | 0.886 | 0.056 |
| Placebo | 3 | 2 hr post ex | 1.475 | 0.192 | 0.745 | 0.078 |
| Placebo | 4 | pre ex | 0.717 | 0.049 | 0.797 | 0.071 |
| Placebo | 4 | 0 post ex | 20.913 | 0.969 | 1.019 | 0.074 |
| Placebo | 4 | 2 hr post ex | 1.450 | 0.190 | 0.699 | 0.060 |
| | | | | | | |
| Supplement | | 0 rest | 0.591 | 0.028 | 0.629 | 0.105 |
| Supplement | 1 | pre ex | 0.673 | 0.038 | 0.759 | 0.067 |
| Supplement | 1 | 0 post ex | 1.900 | 0.302 | 0.885 | 0.059 |
| Supplement | 1 | 2 hr post ex | 0.682 | 0.038 | 0.739 | 0.060 |
| Supplement | 2 | pre ex | 0.670 | 0.050 | 0.762 | 0.068 |
| Supplement | 2 | 0 post ex | 16.543 | 2.561 | 0.823 | 0.065 |
| Supplement | 2 | 2 hr post ex | 1.020 | 0.145 | 0.660 | 0.073 |
| Supplement | 3 | pre ex | 0.655 | 0.031 | 0.795 | 0.067 |
| Supplement | 3 | 0 post ex | 20.914 | 0.762 | 0.913 | 0.062 |
| Supplement | 3 | 2 hr post ex | 1.355 | 0.278 | 0.685 | 0.069 |
| Supplement | 4 | pre ex | 0.722 | 0.060 | 0.798 | 0.078 |
| Supplement | 4 | 0 post ex | 19.329 | 2.100 | 0.909 | 0.047 |
| Supplement | 4 | 2 hr post ex | 0.911 | 0.090 | 0.672 | 0.056 |
| | | | 7.6% lower | | 10.8% lower | |
| | | | 37.1% lower | | 3.9% lower | |

**0=baseline
**1=2mile gallop
**2=1/4 mile work
**3=3/8 mile work
**4=3/8 out of the 1/2 mile work

FIG. 1

| CoQ10 | | | |
|---|---|---|---|
| CTI# | Sample ID | Description | Total CoQ10 mcg/ml |
| 1 | 5A | Horse Serum | 0.103 |
| 2 | 5C | Horse Serum | 0.177 |
| 3 | 5E | Horse Serum | 0.192 |
| 4 | 6A | Horse Serum | 0.103 |
| 5 | 6C | Horse Serum | 0.268 |
| 6 | 6E | Horse Serum | 0.313 |
| 7 | 8A | Horse Serum | 0.068 |
| 8 | 8C | Horse Serum | 0.092 |
| 9 | 8E | Horse Serum | 0.086 |
| 10 | 12A | Horse Serum | 0.077 |
| 11 | 12C | Horse Serum | 0.115 |
| 12 | 12E | Horse Serum | 0.151 |
| 13 | 19A | Horse Serum | 0.062 |
| 14 | 19C | Horse Serum | 0.143 |
| 15 | 19E | Horse Serum | 0.103 |
| 16 | 22A | Horse Serum | 0.090 |
| 17 | 22E | Horse Serum | 0.103 |
| 18 | 22E | Horse Serum | 0.203 |
| 19 | 1A | Horse Serum | 0.077 |
| 20 | 2A | Horse Serum | 0.074 |
| 21 | 3aA | Horse Serum | 0.116 |
| 22 | 11A | Horse Serum | 0.057 |
| 23 | 24A | Horse Serum | 0.059 |
| 24 | 25A | Horse Serum | 0.059 |
| Detection Limit: .005 mcg/ml | | | |
| Method Reference: In-House HPLC BF-05, CoQ10 (Total) | | | |
| Signature of Authorized Personnel: | Date: | | 12/22/2011 |

FIG. 2

Mean and Standard Deviation of CoQ10 Results by Group

Mean and Standard Deviation of Groups

| Treatment | Group 1 Baseline | | Group 2 Baseline | Group 2 Post-30 days | Group 2 Post-60 days |
|---|---|---|---|---|---|
| | μg/mL | | μg/mL | μg/mL | μg/mL |
| Mean | 0.084 | | 0.074 | 0.156 | 0.197 |
| SD | 0.017 | | 0.022 | 0.062 | 0.077 |

FIG. 3

EQUINE NUTRITIONAL SUPPLEMENT

This application claims the priority of Application Ser. No. 61/433,742 filed on Jan. 18, 2011.

BACKGROUND OF THE INVENTION

1. Field of the Invention

The present invention relates generally to nutritional supplements for humans, animals, and, more particularly, to nutritional supplements for equines, and even more particularly for racehorses.

2. Description of the Prior Art

The training of horses for racing and other competition generally begins when the animals are about one year old. As is well known to those of ordinary skill in this field, these so-called yearlings are generally quite susceptible to injury to the joints and soft tissues. It is an unfortunate fact that approximately 60% of yearlings sustain such injury during their initial training and exercise, and, as a consequence, never race competitively.

Further, it is also common for horses to suffer lung bleeds and nosebleeds during training. The nosebleeds are caused by bleeding in the nasal passages and lungs of the animals resulting from increased blood pressure caused by the exertion. Often, a diuretic, such as furosemide, is administered to the horses in an attempt to lower the blood pressure during exertion. Furosemide is available from many manufacturers, one of them being Sanofi-Aventis of Frankfurt am Main, Germany. Sanofi-Aventis markets furosemide under the name LASIX®, which is a registered trademark it owns. Similar negative consequences to training occur in other performance animals such as racing dogs and human athletes and performance athletes.

The present invention presents a fresh approach toward a solution to this problem utilizing a combination nutritional supplement which alleviates inflammation caused by training and high performance activities, provides for faster recovery from training depletion, micro-injury, stress and provides enhanced mitochondrial energy during training and performance.

SUMMARY OF THE INVENTION

The invention is generally directed to a nutritional supplement adapted for use in horses, other animals and humans involved in training or performance activities which tax their bodies by alleviating inflammation caused by training and high performance activities, providing for faster recovery from training depletion and micro-injury and providing enhanced mitochondrial energy during training and performance.

Another object of the invention is to provide an improved nutritional supplement which can be included in a horse's feed such that the horse has enhanced resistance to traditional injuries associated with the stress of racehorse training and performance, provides for more rapid recovery from the training and performance, and provides greater mitochondrial energy to enhance performance.

Yet another object of the invention is to provide an improved nutritional supplement which allows an athlete, human or animal, to train harder with less breakdown and perform at a higher level.

Still a further object of the invention is to provide an improved nutritional supplement which combats the debilitating effects of stress in animals, performance animals and humans.

The invention accordingly comprises the features of construction, combinations of elements and arrangements of part and processes which will be exemplified in the constructions and processes as hereinafter set forth, and the scope of the invention will be indicated in the claims.

BRIEF DESCRIPTION OF THE DRAWINGS

The present invention will be described below with frequent reference being made to the following figures.

FIG. 1 is study results in tabular form showing the effect of supplementation on lactase and MDA in the blood;

FIG. 2 is a tabulated result of a second study conducted testing Coenzyme Q10;

FIG. 3 is a second table showing mean and standard deviation data in connection with Coenzyme Q10 levels for the study results of the study of FIG. 2;

DETAILED DESCRIPTION OF THE PREFERRED EMBODIMENTS

Figure 4:
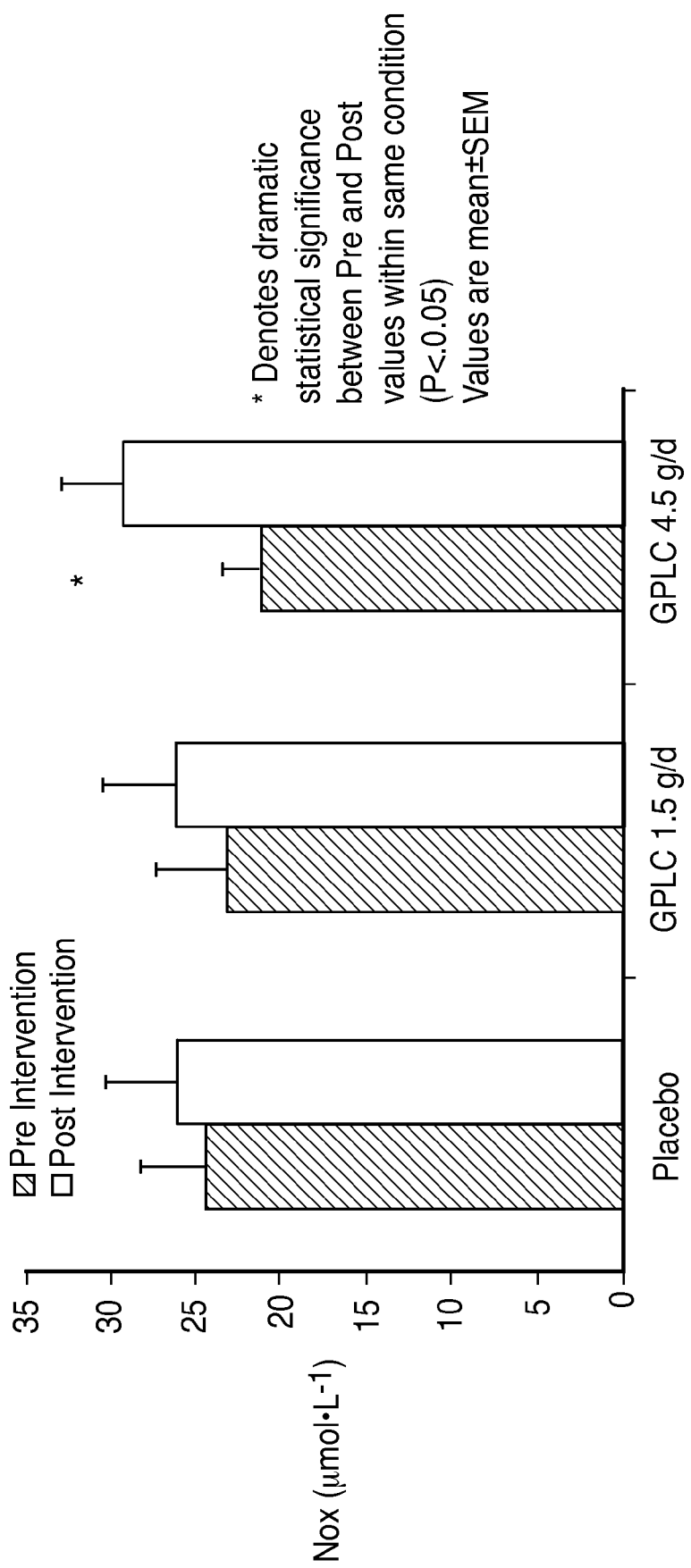
FIG. 4 represents a table in connection with another study in which Carnitine was provided showing the effect of Carnitine supplementation on nitric oxide levels.

In accordance with the present invention, a mixture of Coenzyme Q10, Carnitine, and d-Ribose is used instead of a diuretic, such as LASIX®, as a mitochondrial powerhouse to energize the horses being trained, helping them to run faster and longer by maintaining optimum mitochondrial functioning and peak performance, as well as a far faster recovery with less stress during and after workouts or performance.

In addition, Curcumin and Boswellia extract are added to this mixture to maintain healthy joints and muscles, and to reduce inflammation throughout the bodies of the horses. These additional ingredients may also help prevent unnecessary joint, muscle and soft-tissue injuries and harm due to inflammation which may also damage the internal organs.

A current example of the nutritional supplement is set forth below:

| Ingredient | Amount |
| --- | --- |
| Curcumin | 1.6 g |
| Boswellia extract | 1.6 g |
| d-Ribose | 20 g |
| Carnitine | 8.0 g |
| Coenzyme Q10 | 800 mg |

The amounts and ratios of the ingredients are associated with a formulation intended for use with horses. Varying ratios and amounts of the noted ingredients can be used to tailor the nutritional supplement to the specified recipient, whether equine, other animal or human.

In a preferred embodiment of the invention the proportion of Coenzyme Q10 is preferably between about 400 and 2,000 milligrams, the proportion of the d-Ribose is between about 10 and 30 grams, the amount of Glycine Propionyl L-Carnitine Hydrochloride is between about 4 and 16 grams, the amount of Curcumin is between about 0.8 and 3.2 grams and the amount of Boswellia extract is between about 0.8 and 3.2 grams.

In one preferred embodiment the amount of the five main ingredients are as shown in the table above. In another current preferred embodiment of the invention, the amount of the ingredients are as shown in the table above except that the amount of Carnitine is increased to 12 grams and the amount of Coenzyme Q10 is increased to 1,200 milligrams.

Curcumin is commercially available from a variety of sources including DolCas Biotech, LLC of Chester, N.J. where it is marketed under the trademark BCM-95®; Boswellia is a fragrant resin from a genus of trees known for their many pharmacological uses particularly as anti-inflammatories. Boswellia extract is available from a variety of sources including DolCas Biotech where it is marketed under the trademark BOSPURE®. Both BCM-95® and BOSPURE® are registered trademarks owned by DolCas Biotech.

Ribose comprises the backbone of RNA, a biopolymer that is the basis of genetic transcription. It is related to deoxyribose, as found in DNA. Once phosphorylated, Ribose can become a subunit of ATP, NADH, and several other compounds that are critical to metabolism. d-Ribose is currently commercially available in the United States only from Bioenergy Life Science, Inc. of Ham Lake, Minn.

Carnitine, or, more particularly, Glycine Propionyl L-Carnitine Hydrochloride, and any other L-Carnitine forms, salts and isomers thereof, is an amino acid derivative. Glycine Propionyl L-Carnitine Hydrochloride USP is commercially available from Sigma-tau Health Science, Inc. of Gaithersburg, Md., as marketed under the trademark GLYCOCARN®, a registered trademark owned by Sigma-tau. In addition, Acetyl L-Carnitine, Propionyl L-Carnitine, Carnitine Taurine Complex and other salts and isomers can be used as a substitute for the Carnitine.

Finally, coenzyme Q10 Coenzyme Q10, also known as ubiquinone, ubidecarenone, coenzyme Q, Q10, or Q, is a 1,4-benzoquinone, where Q refers to the quinone chemical group, and 10 refers to the number of isoprenyl chemical subunits in its tail.

This oil-soluble, vitamin-like substance is present in most eukaryotic cells, primarily in the mitochondria. It is a component of the electron transport chain and participates in aerobic cellular respiration, generating energy in the form of ATP. Ninety-five percent of the human body's energy is generated this way. Therefore, those organs with the highest energy requirements—such as the heart, liver and kidney—have the highest CoQ10 concentrations. There are three redox states of Coenzyme Q10: fully oxidized (ubiquinone), semiquinone (ubisemiquinone), and fully reduced (ubiquinol). A particularly bioavailable form of Coenzyme Q10 is commercially available from Tishcon Corp. of Westbury, N.Y., marketed under the trademark HYDROQSORB®, this being a registered trademark owned by Tishcon Corp.

The nutritional supplement in a current preferred embodiment is in the form of a powder, and may be supplied and made available in packets containing the mixture in the amounts appearing in the table above for one administration or dose or in other forms. The nutritional supplement may be administered by mixing it with the feed given to the horse. For example, oats may be mixed with molasses by applying an amount of the molasses to the top of the oats. The contents of the packet of the nutritional supplement is then added, and mixed together with the oats and molasses and rolled into a ball and fed to the horse. The result is a light, sticky feed held together by the molasses, which ensures that the powdered nutritional supplement does not settle-out, but clings to the oats and is completely consumed by the horse.

For daily maintenance, the nutritional supplement may be given to the horse once daily in the morning. When the horse is being trained or is being run at peak performance, the nutritional supplement may be given to the horse once early in the morning, and then again a second time prior to the training or peak performance. When the horse has joint, muscle, or tissue structure injuries or problems, the nutritional supplement may be given to the horse once early in the morning; when the injuries or problems are extreme or severe, the nutritional supplement may be given to the horse a second time in the afternoon or with the evening feeding.

Different dosing regimes are adapted to the needs of other types of animals and humans and their usual eating habits. The formulation is suitable for use in combination with the regular food of the horses, other animals and humans. In humans the nutritional supplement can also be formulated to be provided separately. In animals which are under stress due to transportation or confinement in pens with other animals the nutritional supplement can reduce the effects of the stress on the animal.

This unique formula has a dual purpose. The first is as a nutritional supplement to reduce joint, muscle and soft tissue injuries. The second is as a peak-performance formula, specifically, an energy and recovery powerhouse with powerful anti-inflammatory factors, the latter being provided by the Curcumin and Boswellia extract included in the mixture, while the d-Ribose, Carnitine, and Coenzyme Q10 provide enhanced factors needed by the horse for performance, energy, endurance and faster recovery with far less stress to the horse. Similar forms of delivery and effects are achieved with other animals and with humans.

The inventors designed and sponsored an equine nutriceutical study which has been conducted on a group of 25 racehorses in collaboration with established research universities. The equine nutriceutical study was designed to determine if a nutriceutical with ATP energy support could impact inflammatory mediators, cytokines and RNA expression. Since horses in training usually develop joint, tendon, ligament and muscle problems, it was suspected that these animals would demonstrate higher serum inflammatory mediators induced by the inflammation of tissues that accompanies the training process. Although equines have been studied in the laboratory setting (treadmills), no other study has ever been done demonstrating an increase in inflammatory mediators in a training facility or on a racetrack and subsequent blunting of these cytokines following nutritional supplementation. Our study group expected to see a rise in inflammatory mediators with training and a fall in the group that was supplemented with nutritional supports. The study included 25 equines and was supplemented in a double-blinded Placebo Controlled Study where neither the trainers, handlers nor those providing the supplement knew whether a particular horse was receiving the nutritional supplement or a placebo. Half the group was put on placebo and the other half was given a formula containing Coenzyme Q10, PLC Carnitine, Ribose, Boswellia extract and Curcumin. The hypothesis proved to be correct in that the study group had a statistically significant downsizing of the inflammatory mediators. The investigation is continuing to look at lipid peroxides as a measure of oxidative stress as well as malondialdehydes (MDAs) to see if the horses given nutritional support also had reduction in these parameters. It is expected that the lipid peroxides and MDAs will be lower in the group given the nutriceuticals.

This study has demonstrated a reduction in inflammatory cytokines after 65 days of gradual increments in training. A larger 1 to 2 year old study in the same group of horses will look at joint/ligament breakdown, tendonitis, hoof and hock problems, laminitis and even pulmonary/vascular congestion. It appears from the results so far that the formula will: not only decrease inflammation and possibly even structural breakdowns in the equine; reduce the need for pharmaceutical drugs, i.e., Lasix, phenylbutazone, ACTH, etc.; and also improve performance as well. It was noted and recorded, anecdotally, that there was an improved energy, performance, faster recovery of the horses after stressful workouts and training, for those horses given the nutritional supplement during the study. Those anecdotal reports were from the farm manager who makes entries about horses which were subsequently matched with the horses who received the supplement.

It has been demonstrated in numerous studies that there are increases in expression of inflammatory cytokines both in the muscles and peripheral blood of horses following treadmill exercise. These studies for example showed that the Blood TNF-alpha levels went from about 15 up to as much as 25-30 in the period six hours after the exercise, and not returning to baseline even after 24 hours. Direct measurement of this sort of type of marker in a statistically significant number of horses in training without a treadmill is somewhat more difficult. Therefore, it was determined that the presence in the blood of the inflammation mediator Malondialdehyde ("MDA") would be a suitable indirect way to measure the degree of exercise induced inflammation. This has the benefit of being measurable in blood. Similarly, the presence of CoQ10 in the blood is a good indication of the endurance and performance of the horses. An increased level of CoQ10 has been shown to relate to enhanced strength and endurance in horses and humans. The presence of the Coenzyme Q10, Carnitine and d-Ribose act as a mitochondrial powerhouse to increase the energy and endurance of the horses. The Curcumin and boswellin act to help maintain healthy joints and muscles and to reduce the inflammation throughout the bodies of the horses.

A second study was conducted utilizing the information learned from the first study and to utilize the above methods, in which a series of equines were provided a nutritional supplement and tested for their levels of Coenzyme Q10 and for the inflammation mediator Malondialdehyde ("MDA"). In two and three year old racehorses the most common cause of diminished performance is lameness which relates to exercise induced inflammation and joint injuries due to exercise. The one year old horses are not yet raced (which begins at ages two and three). Nevertheless there is very significant loss of training time for horses due to the lameness issues. The study was intended to test both for the presence of CoQ10 in the blood as a marker for mitochondrial energy and for performance and for the presence of MDA which would be a marker of exercise induced inflammation. The horses tested were one year old horses who were provided with either a placebo or the studied nutritional supplement which included Coenzyme Q10, Carnitine, d-Ribose, Boswellin and Curcumin. The nutritional supplement was mixed with the horses' regular feed, in the morning and evening feeds in a way which assured that the horses would consume the full amount of the nutritional supplement. The horses were provided with one packet of the nutritional supplement during the first 30 days of the study and then two packets of the nutritional supplement during the second 30 days of the study.

The Study, results of which are shown in tabular form in FIG. 1 reflect that for the horses provided the nutritional supplement in accordance with the invention there was a significant reduction in the lactase in the blood and in the presence of MDA both pre and post exercise.

The table shown in FIG. 1 shows the plasma lactate and MDA data for horses receiving a placebo, of which there were 12 horses, and those receiving the dietary supplement, of which there were 11 horses. The data shows that the lactate in the placebo receiving horses both post exercise and 2 hours post exercise were significantly higher than that of the supplemented horses. As shown, the post exercise lactate was 7.6% lower in the supplemented horses and 2 hours post exercise was 37.1% lower. This is indicative of the horses' recovering more quickly and not being as muscularly tired following the workout. Similarly, the data for the MDA, both the means data and the standard error of the mean (SEM) data show that both post exercise and 2 hours post exercise there was a significant lowering in the MDA, which is a mediator of inflammation across the board with these supplemented horses. These supplemented horses had a mean reduction in MDA post exercise of 10.8% and a 3.9% lower MDA 2 hours post exercise.

With reference to FIG. 2, we note that a separate study was conducted in which horses were supplemented with Coenzyme Q10 and the results were tabulated as shown in FIG. 2. The test was conducted on 12 horses, of whom 6 were given the placebo and only had their baseline Coenzyme Q10 measured and 6 horses were supplemented and they had the Coenzyme Q10 measured at baseline, after 30 days of supplementation and after 60 days of supplementation. The data is grouped into four separate groups. A group 1 baseline, corresponding to those horses which were given the placebo, a group 2 baseline for those horses which were supplemented with the supplement in accordance with the invention including Coenzyme Q10, the group 2 horses after 30 days of supplementation and, finally, the group 2 horses after 60 days of supplementation. As seen in FIG. 3, annexed hereto, which presents in tabular form the mean and standard deviation data in connection with the Coenzyme Q10 levels found in the studies, it is clear that the supplementation with a nutritional supplements including Coenzyme Q10 as part of the equine nutritional supplement in accordance with the invention resulted in a significant increase in blood levels of Coenzyme Q10 during the period of supplementation. The mean Coenzyme Q10 values are not significantly different between the two groups at baseline, i.e., the supplemented and non-supplemented horses. The mean Coenzyme Q10 levels for the supplemented group significantly increased with time from baseline through 30 days (p=<0.014) and 60 days (p=<0.05) of Coenzyme Q10 intervention.

As previously noted, there is a significant effect that has been noted both through research and empirically that the horses with the higher Coenzyme Q10 levels performed better and recovered more quickly following training. Also, because Coenzyme Q10 is a powerful antioxidant, it is believed that it also had a significant positive effect, which was noted anecdotally, on the health of the horses in the study with decreased lameness and muscle soreness noted by the farm manager during the course of the trial related to horses supplemented with the Coenzyme Q10 filled feed supplement.

Figure 5:
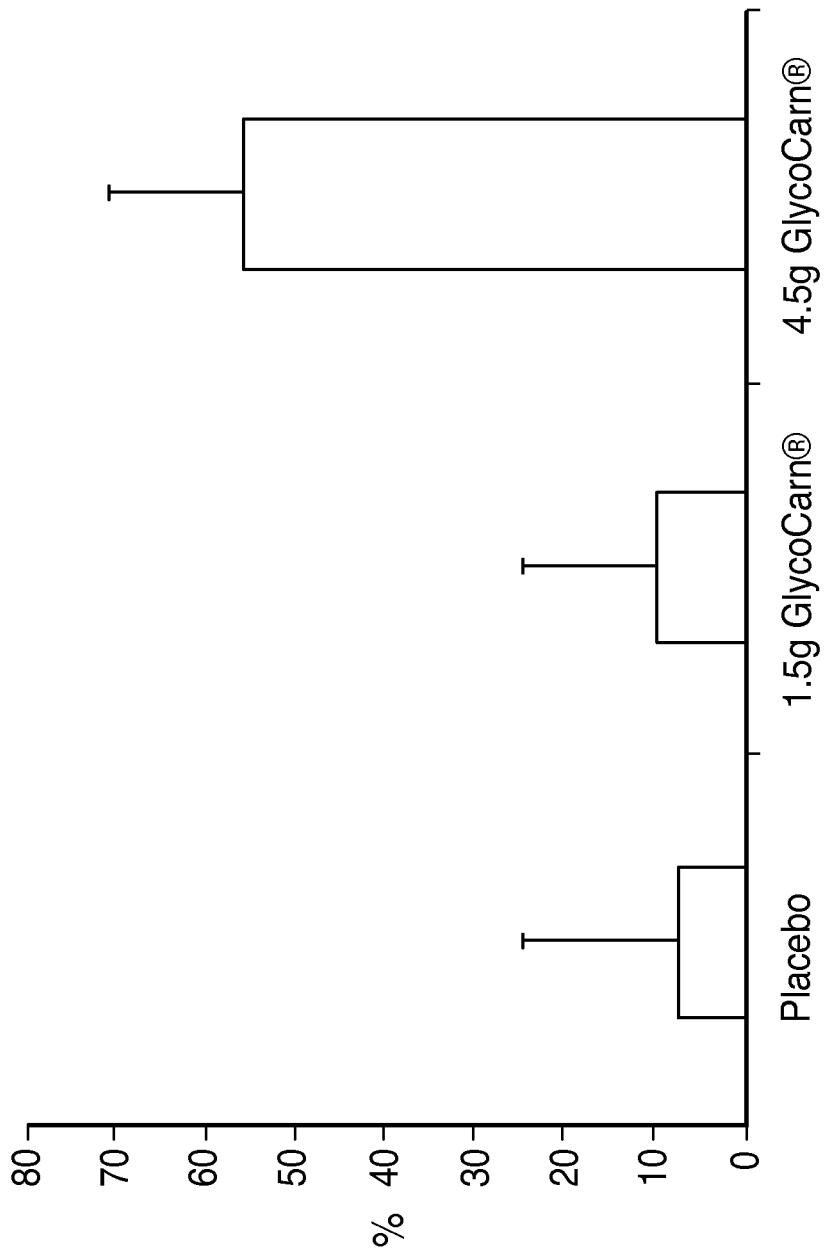
FIG. 5 is a study showing the relative levels of nitric oxide between the placebo and treatment groups for the study shown in FIG. 4.
Figure 6:
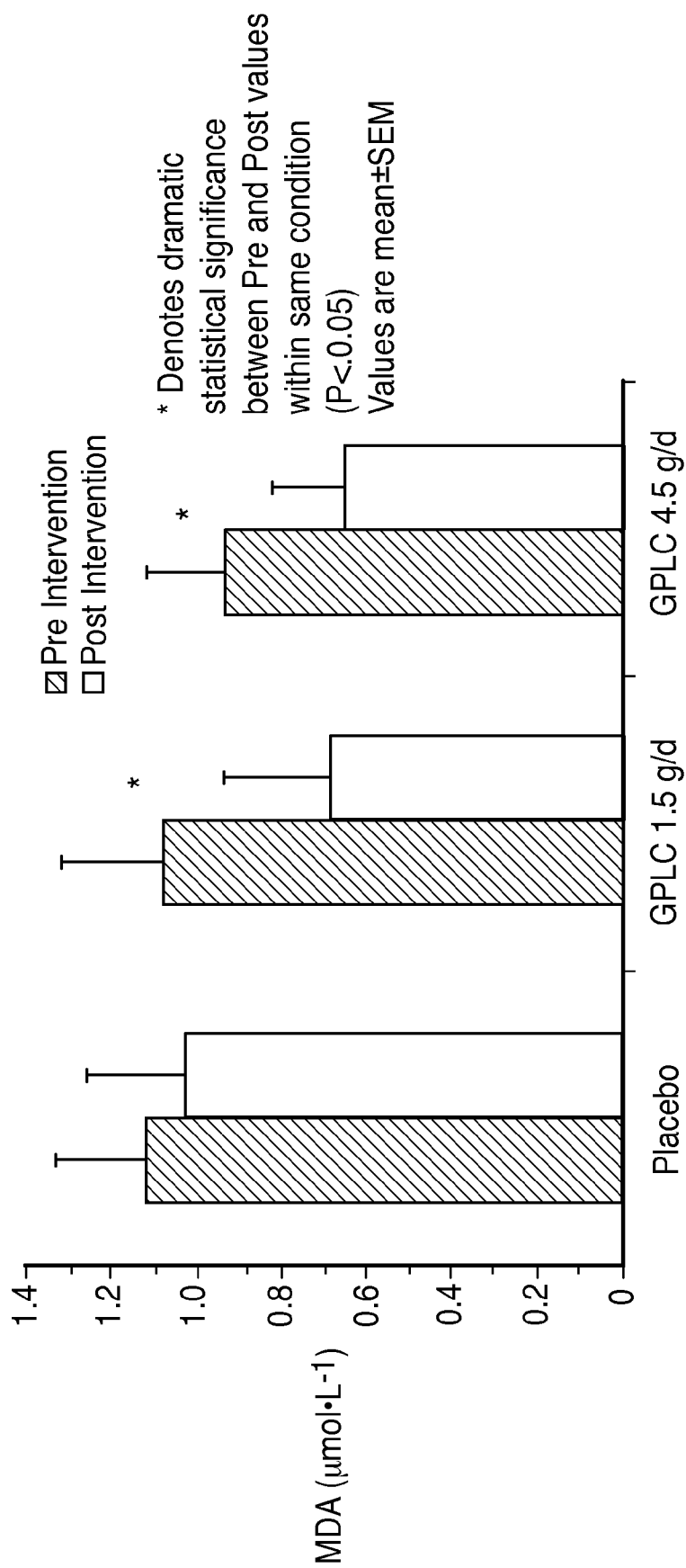
FIG. 6 is a tabular form of results for a study in which Carnitine supplementation was used to determine the effect on MDA in the blood.

It has been studied in humans that the addition of Carnitine, in particular the Glycine Propionyl-L-Carnitine Hydrochloride molecule against a placebo in an exercise study of humans resulted, following 8 weeks of supervised aerobic training, in a significant and dramatic statistical significance between pre-intervention and post-intervention levels of nitric oxide. As shown in FIGS. 4 and 5, a study, in which the Carnitine was given at the level of 1.5 grams per day, and 4.5 grams per day produced statistically significant enhancement in nitric oxide levels in the study subjects. It is believed that the similar pathways and effects are present in equine bodies such that the supplementation with the Carnitine, along with the other elements of the nutritional supplement will produce a similar significant enhancement nitric oxide formation. That study also measures the effect of Glycine Propionyl-L-Carnitine Hydrochloride on lipid peroxidation in human subjects and found statistically significant differences in the presence of MDA for the post-intervention subjects. MDA is a mediator of inflammation in humans and in horses. Again, it is believed that a similar effect in reduction of the inflammatory mediator MDA was found in the horses through study and empiric observation of the horses by the farm manager. The study results for the MDA are found in FIG. 6.

It is known in the literature that nitric oxide in chondrocytes within articular cartilage is inhibited by mechanical stress. (Wiseman M, Henson F, et al (2003). "Dynamic compression strain inhibits nitric oxide synthesis by equine chodrocytes isolated from different areas of cartilage surface." *Equine Vet J.* 35(5): 451-456.) In addition, nitric oxide mediated profusion within the equine hoof may improve lameness during acute laminitis. (Hinkley K A, Fern S, et al (1996). "Nitric oxide donors as treatment for grass induced acute laminitis nitric oxide donors in treatment in ponies." *Equine Vet J.* 28(1): 17-28.)

The nutritional supplement can have different variations of the constituents to enhance particular properties which are to be favored. For example, an improved formula can include the following: Curcumin (BCM 95) 1.6 grams, Boswellia 1.6 grams, d-Ribose 20 grams, GlycoCarn 12 grams, solublized Coenzyme Q10 1.6 grams. This formula is intended to enhance the Coenzyme Q10 and GlycoCarn components to induce a more significant effect. A more modest other formulation would include 1.6 grams of Curcumin, 1.6 grams of Boswellia, 20 grams of d-Ribose, 8 grams of GlycoCarn and 800 milligrams of solublized Coenzyme Q10. In circumstances where one is looking to work only on certain components, a supplement focusing on mitochondrial energy can be utilized centered around the Coenzyme Q10, d and Carnitine, which provide the core elements of the nutritional supplement. Additional formulations in which the Curcumin and Boswellia are added, either separately or together, to this core group are indicated where reduction in inflammation is indicated.

In summary, the present nutritional supplement is a mitochondrial powerhouse which helps to energize and maintain optimum mitochondrial functioning and peak performance during stressful workouts; helps faster recovery after workouts; helps maintain healthy joints, muscles and soft tissues; and may help prevent unnecessary joint, muscle and soft tissue injuries.

It will thus be seen that the objects set forth above, among those made apparent in the preceding description, are efficiently obtained, and, since certain changes may be made in the above construction without departing from the spirit and scope of the invention, it is intended that all matter contained in the above description or shown in the accompanying drawings shall be interpreted as illustrative, and not in a limiting sense.

It is also understood that the following claims are intended to cover all of the generic and specific features of the invention herein described and all statements of the scope of the invention, which, as a matter of language, might be said to fall there between.

What is claimed is:

1. An equine nutritional supplement for increasing cellular energy, enhancing healing, and/or reducing inflammation consisting essentially of:
    2,000 mg of CoEnzyme Q10;
    10,000 mg of d-Ribose;
    4,000 mg of Glycine-Propionyl-L-Carnitine Hydrochloride, or an equivalent salt thereof;
    800 mg of Curcumin; and
    800 mg of Boswellia, Boswellia extract, or Boswellin.

2. A method for increasing cellular energy, enhancing healing, and/or reducing inflammation in a horse in need thereof comprising:
    adding an effective amount of the equine nutritional supplement according to claim 1 to the horse's feed, and
    feeding the supplemented feed to the horse on at least a daily basis.

3. The method of claim 2 wherein the supplemented feed is fed to the horse twice a day.

* * * * *